(12) United States Patent
Sahbaee Bagherzadeh et al.

(10) Patent No.: US 12,059,237 B2
(45) Date of Patent: Aug. 13, 2024

(54) DEEP LEARNING FOR PERFUSION IN MEDICAL IMAGING

(71) Applicant: Siemens Healthcare AG, Forchheim (DE)

(72) Inventors: Pooyan Sahbaee Bagherzadeh, Mount Pleasant, SC (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 733 days.

(21) Appl. No.: 16/512,653

(22) Filed: Jul. 16, 2019

(65) Prior Publication Data
US 2021/0015438 A1    Jan. 21, 2021

(51) Int. Cl.
*A61B 6/00* (2024.01)
*A61B 5/026* (2006.01)
(Continued)

(52) U.S. Cl.
CPC .............. *A61B 5/026* (2013.01); *A61B 6/504* (2013.01); *A61B 6/507* (2013.01);
(Continued)

(58) Field of Classification Search
CPC ..... A61B 6/507; A61B 6/504; A61B 5/02007; A61B 5/7267; A61B 5/743; A61B 6/032; A61B 6/469; A61B 6/5217; A61B 8/065; A61B 8/5223; A61B 2576/00; A61B 8/06; A61B 8/0891; A61B 8/4416; A61B 5/026; A61B 6/481; A61B 6/503; A61B 6/5294; A61B 5/0033; A61B 5/0044; A61B 5/055; A61B 6/00; A61B 6/52; A61B 8/0883; A61B 8/481; A61B 8/52; G06K 9/627;
(Continued)

(56) References Cited

U.S. PATENT DOCUMENTS

2003/0016778 A1* 1/2003 Tachizaki ............... G16H 40/63
378/4
2013/0343513 A1   12/2013 Noo et al.
(Continued)

FOREIGN PATENT DOCUMENTS

CN       107533032 A      1/2018
WO    WO-0175469 A1 * 10/2001 ........... G01R 33/563

OTHER PUBLICATIONS

Akos Varga-Szemes, et al. "CT Myocardial Perfusion Imaging" GE Healthcare Inc. Mar. 2015. pp. 487-497.
(Continued)

*Primary Examiner* — Keith M Raymond
*Assistant Examiner* — Fikirte (Fiki) T Ashine

(57) ABSTRACT

For decision support based on perfusion in medical imaging, a machine-learned model, such as a model trained with deep learning, generates perfusion examination information from CT scans of the patient. Other information, such as patient-specific information, may be used with the CT scans to generate the perfusion examination information. Since a machine-learned model is used, the perfusion examination information may be estimated from a spatial and/or temporally sparse number of scan shots or amount of CT dose. The results of perfusion imaging may be provided with less than the current, standard, or typical radiation dose.

16 Claims, 2 Drawing Sheets

(51) Int. Cl.

| | | |
|---|---|---|
| *A61B 6/50* | (2024.01) | |
| *G06F 18/2413* | (2023.01) | |
| *G06N 20/00* | (2019.01) | |
| *G06T 7/11* | (2017.01) | |
| *G06V 10/764* | (2022.01) | |
| *G06V 10/82* | (2022.01) | |
| *G16H 30/40* | (2018.01) | |
| *G16H 50/20* | (2018.01) | |
| *A61B 5/00* | (2006.01) | |
| *A61B 5/02* | (2006.01) | |
| *A61B 6/03* | (2006.01) | |
| *A61B 6/46* | (2024.01) | |
| *A61B 8/06* | (2006.01) | |
| *A61B 8/08* | (2006.01) | |
| *G06F 18/21* | (2023.01) | |
| *G06F 18/22* | (2023.01) | |
| *G06N 3/02* | (2006.01) | |
| *G06T 7/00* | (2017.01) | |
| *G16H 10/60* | (2018.01) | |
| *G16H 50/50* | (2018.01) | |

(52) U.S. Cl.
CPC ......... *G06F 18/2413* (2023.01); *G06N 20/00* (2019.01); *G06T 7/11* (2017.01); *G06V 10/764* (2022.01); *G06V 10/82* (2022.01); *G16H 30/40* (2018.01); *G16H 50/20* (2018.01); *A61B 5/02007* (2013.01); *A61B 5/7267* (2013.01); *A61B 5/743* (2013.01); *A61B 6/032* (2013.01); *A61B 6/469* (2013.01); *A61B 6/5217* (2013.01); *A61B 8/065* (2013.01); *A61B 8/5223* (2013.01); *A61B 2576/00* (2013.01); *G06F 18/217* (2023.01); *G06F 18/22* (2023.01); *G06N 3/02* (2013.01); *G06T 7/0012* (2013.01); *G06T 2200/04* (2013.01); *G06T 2207/20081* (2013.01); *G06T 2207/30104* (2013.01); *G06V 2201/03* (2022.01); *G16H 10/60* (2018.01); *G16H 50/50* (2018.01)

(58) Field of Classification Search
CPC .. G06K 9/6201; G06K 9/6262; G06K 9/6273; G06N 20/00; G06N 3/02; G06N 3/0445; G06N 3/0454; G06N 3/0472; G06N 3/08; G06T 7/11; G06T 7/0012; G06T 2200/04; G06T 2207/20081; G06T 2207/30104; G16H 30/40; G16H 50/20; G16H 10/60; G16H 50/50; G16H 50/70; G06V 10/42; G06V 2201/03; G06V 2201/031; G06V 2201/10; G06V 10/82

See application file for complete search history.

(56) References Cited

U.S. PATENT DOCUMENTS

| | | | |
|---|---|---|---|
| 2015/0302139 A1* | 10/2015 | Sankaran | A61B 5/7275 703/20 |
| 2016/0000389 A1* | 1/2016 | Heuscher | A61B 6/4035 378/16 |
| 2016/0066800 A1 | 3/2016 | Sharma | |
| 2017/0245821 A1 | 8/2017 | Itu | |
| 2018/0218502 A1* | 8/2018 | Golden | G06T 7/11 |
| 2018/0240219 A1* | 8/2018 | Mentl | G06N 3/08 |
| 2018/0253531 A1 | 9/2018 | Sharma et al. | |
| 2018/0315505 A1* | 11/2018 | Itu | G16H 10/20 |
| 2020/0286614 A1* | 9/2020 | Do | G06N 7/01 |
| 2022/0087631 A1* | 3/2022 | d'Esterre | A61B 6/027 |

OTHER PUBLICATIONS

Juarez-Orozco, Luis Eduardo, et al. "Machine Learning in the Evaluation of Myocardial Ischemia Through Nuclear Cardiology." Current Cardiovascular Imaging Reports 12.2 (2019): 5. pp. 1-5.
Spier, Nathalia, et al. "Classification of Polar Maps from Cardiac Perfusion Imaging with Graph-Convolutional Neural Networks." Scientific reports 9.1 (2019): 7569. pp. 1-8.

* cited by examiner

DEEP LEARNING FOR PERFUSION IN MEDICAL IMAGING

BACKGROUND

The present embodiments relate to perfusion examination in medical imaging. In cardiac imaging, perfusion imaging images both the detailed anatomy and function of the heart at the same time. Computed Tomography (CT)-based perfusion imaging may provide advantages. For example, CT perfusion imaging may reduce healthcare costs by eliminating some hospital stays, cutting the number of tests, and/or speeding patient diagnosis. These advantages are offset by risks from exposure of the patient to x-ray radiation in CT imaging. Since perfusion imaging measures concentration of contrast agent over time, the patient is exposed to more x-ray radiation due to the repetition in scanning.

SUMMARY

By way of introduction, the preferred embodiments described below include methods, systems, instructions, and non-transitory computer readable media for decision support based on perfusion in medical imaging. A machine-learned model, such as a model trained with deep learning, generates perfusion examination information from CT scans of the patient. Other information, such as patient-specific information, may be used with the CT scans to generate the perfusion examination information. Since a machine-learned model is used, the perfusion examination information may be estimated from a spatial and/or temporally sparse number of scan shots or amount of CT dose. The results of perfusion imaging may be provided with less than the current, standard, or typical radiation dose.

In a first aspect, a method is provided for estimating myocardial perfusion by a medical imager. A computed tomography (CT) system scans a patient. The scanning provides coronary CT data representing contrast agent in a heart of the patient over time. Information for the patient in addition to the coronary CT data is acquired. A machine-learned model having been trained by deep learning estimates the myocardial perfusion. The machine-learned model outputs the myocardial perfusion in response to input of the coronary CT data and the information. The myocardial perfusion is displayed, such as a quantity or image.

In one embodiment, fewer than five shots are used in the scanning. The estimation is performed in response to input of the coronary CT data from no more than the five shots. In other embodiments, the scanning uses less than ½ an effective dose given a scanning protocol. The estimation is performed in response to input of the coronary CT data corresponding to no more than the effective dose.

Various types of patient information may be acquired for estimation. For example, patient attributes for the patient are acquired. Patient attributes are clinical information, such as weight, height, body mass index, sex, age, or measures of performance (e.g., cardiac output). As another example, a CT angiography image of the patient is acquired. In yet another example, arterial enhancement curve information for the patient is acquired. The arterial enhancement curve may be different for different patients due to blockage or other disease changing the flow of contrast agents in the arteries, where the differences in flow result in different timing and/or amounts of contrast agent for myocardial perfusion. As yet another example of patient information, a static myocardial measure for the patient is acquired. The peak perfusion or other perfusion quantification at a given time or upon a given event may be calculated and input.

The machine-learned model estimates by input of different information, such as the patient information, the coronary CT data, and an injection protocol parameter. The injection protocol parameter characterizes the injection of contrast agent used for the patient, such as the type, rate, volume, and/or location of contrast agent injection.

Various types of outputs may be generated. For example, the myocardial perfusion is estimated as a parametric image. Any perfusion quantity, such as time to peek perfusion, data point values, or other perfusion curve characterization, is determined for each spatial location and an image generated for that parameter. As another example, the myocardial perfusion is estimated as a perfusion quantity, such as a peak, time-to-peak, blood flow, blood volume, mean transit time, or combination thereof. In other embodiments, an image processor determines a diagnosis or therapy from the estimated myocardial perfusion and/or from application of the machine-learned model. The diagnosis or therapy conclusion or recommendation may be displayed.

Various types of machine-learned models may be used. For models learned with deep learning, the machine-learned model may be a convolutional neural network, a generative network having been trained adversarially, or a recurrent neural network.

In a second aspect, a system is provided for decision support based on perfusion in medical imaging. A computed tomography (CT) scanner is provided for scanning a patient while contrast agent is in the patient. The CT scanner is configured to output CT data for the patient. The CT data is from a sequence of six or fewer scan shots and represents the contrast agent. A memory is configured to store a machine-learned model. An image processor is configured to estimate perfusion information by input of the CT data and patient-specific information to the machine-learned model. The perfusion information is provided with no more than the six or fewer scan shots of the CT data to represent the contrast agent. A display is configured to display the perfusion information.

In one embodiment, the CT scanner is configured to scan the patient with an effective dose less than ½ used to scan given a scanning protocol for perfusion for the six or fewer scan shots. The image processor is configured to estimate the perfusion information based on no more than the effective dose.

In an embodiment, the image processor is configured to estimate by input of the CT data, the patient-specific information, and injection protocol information for injection of the contrast agent into the patient. In yet other embodiments, the patient-specific information is a patient attribute, an angiography image, an arterial enhancement curve, and/or quantification from the CT data. The perfusion information generated by the machine-learned model may be a perfusion image, a quantitative value of perfusion, a diagnosis, and/or a therapy.

In a third aspect, a method is provided for decision support based on perfusion measured by a medical imager. A computed tomography (CT) system scans a patient. The scanning provides CT data representing contrast agent in the patient over time acquired with a CT dose index of 80 or lower. Perfusion examination information is generated by a machine-learned model applied to the CT data. The perfusion examination information may be a perfusion image, perfusion quantification, or an end result of the examination (e.g., diagnosis and/or therapy). The perfusion examination information is output.

In one embodiment, a diagnosis and/or therapy as the perfusion examination information. In another embodiment, the machine-learned model is a deep-learned neural network applied to the CT data and personalized patient information.

The present invention is defined by the following claims, and nothing in this section should be taken as a limitation on those claims. Features or aspects for one type of claim (e.g., method or system) may be used in another type of claim. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Deep learning-based myocardial perfusion decision support is provided. The deep learning-based support potentially addresses the limitation of the current CT perfusion techniques by reducing the necessary number of the scan shots and images from the patient. The Artificial Intelligence (AI) provides perfusion information (e.g., dynamic myocardial perfusion) with the same performance of a regular perfusion test and reduced radiation dose and scan time. Such an approach may result in dose and/or time reduction. For example, tissue perfusion (e.g., myocardial perfusion) is determined with reduction in radiation dose for CT and scan time since a temporally and/or spatially sparse perfusion measures as compared to a standard perfusion CT imaging may be acquired and the model may determine the missing information and/or perfusion results without the full sampling.

One example application used herein is myocardial CT perfusion examination. The AI-enhanced perfusion examination may be used in other modalities than CT, such as in MR. The AI-enhanced perfusion examination may be used for non-cardiac perfusion imaging, such as neuro perfusion or perfusion study of the liver or other organs or tissue.

Figure 1:
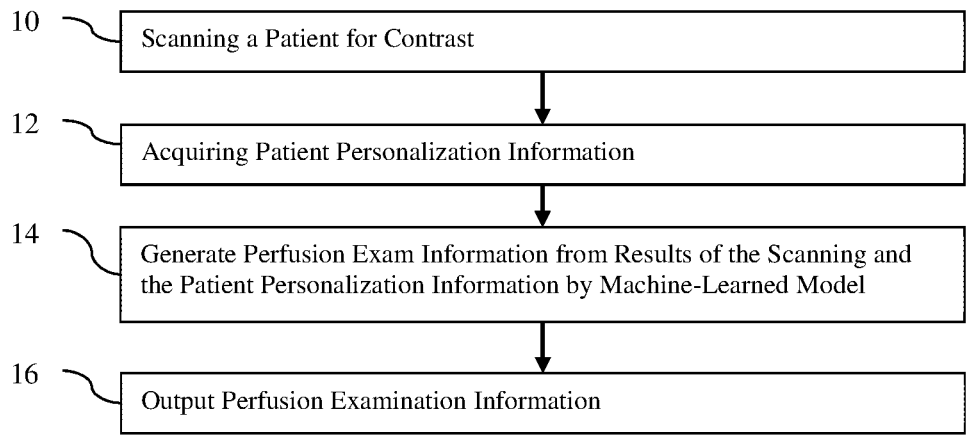
FIG. 1 is a flow chart diagram of one embodiment of a method for decision support based on perfusion measured by a medical imager.

FIG. 1 is a flow chart of one embodiment of a method for decision support based on perfusion measured by a medical imager. In one embodiment, the method is for estimating myocardial perfusion. In other embodiments, the method provides other perfusion examination information, such as a diagnosis or therapy recommendation for an end-to-end approach. A machine-learned model is used to generate the estimation or information, allowing for perfusion examination decision support using a shorter scan time and/or less dose.

A medical scanner performs the acts. Alternatively or additionally, a workstation, server, or other computer performs one or more of the acts. In one embodiment, the system of FIG. 3 performs the acts. For example, a CT scanner performs act 10. An image processor performs acts 12, 14, and 16. Other devices may perform or be used in performance of any of the acts.

The acts are performed in the order shown (e.g., top to bottom or numerical) or other orders. For example, acts 10 and 12 are performed in any order.

Additional, different, or fewer acts may be provided. For example, the method is performed without act 12 and/or act 16. As another example, acts for configuring a medical scanner are provided. In yet another example, acts for using the generated output are provided.

In act 10, a sequence of medical images or datasets are acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format (i.e., scan or voxel data). As another example, the medical image may be a plurality red, green, blue (e.g., RGB) values output to a display for generating the image in the display format. The medical image may not yet be a displayed image, may be a currently displayed image, or may be previously displayed image in the display or other format. The image or imaging is a dataset that may be used for anatomical imaging, such as scan data representing spatial distribution of anatomy (e.g., coronary arteries) of the patient. Medical data, such as image data or other data from the scan, is acquired.

The medical data is obtained by loading from memory and/or transfer via a computer network. For example, previously acquired scan data is accessed from a memory or database. As another example, scan data is transmitted over a network after acquisition from scanning a patient. In other embodiments, the medical image or scan data is obtained by scanning the patient.

Any type of medical data may be used. In one embodiment, a CT scanner or system acquires CT data representing a patient and contrast agent in the patient. CT data is acquired by rotating a source of x-rays and an opposing detector about a patient. Any range and/or path of travel may be used, such as rotating along a helical path of travel. During scanning, a number of scan shots are acquired. Each scan shot is a cross-sectional image acquisition each time the CT scanner x-ray tube is on. In order to collect iodine distribution information at different time points during the first path of contrast agent, multiple scan shots (e.g., 10) are acquired.

C-arm or another x-ray imaging may be used instead. Computed tomography is then used to determine the two or three-dimensional distribution of x-ray attenuation from the projections detected by the detector.

Any number of scan shots or readings from the detector may be used. To obtain a sequence of CT data representing the patient and contrast agents at different times, the scan is repeated. Each repetition of the scanning to acquire data for a given time is a scan shot.

In other embodiments, other types of scan data or medical images are obtained, such as magnetic resonance, x-ray, ultrasound, positron emission tomography (PET), single photon emission computed tomography (SPECT), or other medical imaging modality.

In one embodiment, CT scanning is performed to acquire the coronary or other CT data representing a heart or coronary region of the patient. Other coronary CT data may be acquired, such as Dual Energy or Photon Counting data.

Based on the received detected intensities, a three-dimensional representation of the patient (i.e., the density or absorption as a function of voxel or location) and contrast agent is generated by computed tomography processing. Alternatively, the scan data represents a two-dimensional cross-section of the patient. Data representing an interior region of a patient is obtained. Some of the data from each scan shot is responsive to contrast agent in the patient. The frame of data represents a two or three-dimensional region of the patient and contrast agent. Values are provided for each of multiple locations distributed in two or three dimensions. By repetition, a sequence of frames of data or images are generated to show the perfusion or contrast agent at different times. CT perfusion sequential images are obtained.

While any number of scan shots and/or dosage may be use used in acquiring the sequence of CT images representing perfusion, a reduced number may be desirable. Rather than using a standard, current, or higher number of scan shots or dosage, a lower spatial and/or temporal sampling is performed. For example, fewer than 10, 8, 5 or other number of scan shots are used over a period of 5, 10, 20, 30, or other number of seconds. Rather than using 10-15 scan shots and corresponding images, fewer are used. Given any standard or common number of scan shots for a protocol, fewer scan shots may be used. The same or even greater number of scan shots may be used with a lesser spatial sampling. For example, the field of view is divided into parts and different sets of scan shots are performed for the different parts rather than full spatial sampling for each scan shot. As another example, a reduced number of slices are scanned.

The temporal and/or spatial sparsity allowed by using AI-based examination allows for a reduced CT dose index. Rather than the 200 or more CT dose index typical for myocardial perfusion, the dose index is 100, 80, 70, 50 or other number. For any standard, guideline, or scan protocol in perfusion imaging, new technologies (e.g., detectors or tube current modulations) may reduce the radiation dose. Further reduction, such as by 50-80%, of the dose from that standard, guideline, or scan protocol not using machine-learned based perfusion information may be reduced using the AI. The effective dose for CT perfusion varies depending on the specific acquisition protocol, such as 2.5-21 mSv with an average radiation exposure of 12 mSv. Combined dynamic rest and stress CT perfusion studies may use radiation exposer of about 18 mSv. Using AI, only 9 mSv may be used with a dose of, for example, 100 mGy, instead of the 18 mSv, representing a 50% reduction in effective dose. 40-60% or other reduction in effective dose may result given an acquisition protocol and dose in common but using AI to predict some perfusion. By using lower radiation dosage without reducing the intensity of the x-rays, the patient is exposed to less radiation. Rather than a corresponding decrease in diagnostic value, the reduction is provided since the machine-learned model may output information even with sparse sampling.

Other information may be gathered. For example, injection protocol parameters are obtained. The rate, volume, type of contrast agent, location of injection, or other characteristics of the injection of the contrast agent is obtained, such as from a medical record for the patient or a radiology database. The information about the contrast agent and agent injection used for the patient is obtained.

In act 12, the image processor acquires information for the patient in addition to the coronary CT data. Patient-specific information is acquired by mining, loading, input, or another source. For example, patient-specific information is loaded from a computerized medical record for the patient and/or solicitation of input from a user.

By obtaining patient-specific information, personalized information may be used. Such personalization enables estimation or generation of perfusion examination information based on similarity to other patients.

Various types of patient-specific information may be acquired. For example, patient attributes are acquired for the patient being scanned. The size, age, sex, cardiac output, other clinical measures, other characteristics of the patient's body, medical history, family medical history, and/or genetics are acquired as patient attributes. Non-image information is acquired.

As another example, an angiography image of the patient is acquired. The CT scanner may acquire the angiography image, or the image may be from another source (e.g., stored image taken at a different time and/or with a different modality). The angiography image itself may be used for input to the machine-learned model. Alternatively, features are extracted from the angiography image, such as anatomical and plaque related features. The extracted features are then input.

In yet another example, arterial enhancement curve information for the patient is acquired. The CT scanner or other imager (e.g., ultrasound) may scan one or more arteries. The rate, volume, volume flow, velocity, change over time, and/or other information from arterial enhancement by the injection bolus of the contrast agent in the patient are determined. This arterial enhancement curve information may indicate restriction, disease, and/or other patient-specific information that effects the perfusion.

As another example, a static myocardial perfusion measure for the patient is acquired. The CT data over time shows dynamic perfusion. For scanning at rest, a CT angiography image may be used to acquire CT perfusion. For stress, the CT scan is used. The perfusion at a given time, such as a set time after arrival of contrast agent or at the peak perfusion, may be used to determine a quantity for static perfusion. For example, the peak value by location or an average for the dataset, the time to peak, or other measure or quantification of perfusion is determined from the sequence of CT data. The static perfusion may be from the peak enhancement. This static measure may be used as patient-specific information for input to the machine-learned model.

Other sources of patient-specific information may be used. For example, a physics or other model of anatomy may be fit to scan data representing anatomy of the patient. The personalized or fit model is then used to model operation of the anatomy, such as to calculate flow characteristics in the heart or vessels. Functional and/or physiological models may be used. The calculated values from the modeling, such as physics-based validated estimated values, may be used as inputs to the machine-learned model.

In act 14, the image processor generates perfusion examination information. The CT data representing the contrast agent over time in the patient with or without other information (e.g., patient-specific information and/or values for injection protocol parameters) is input to a machine-learned model, which outputs the perfusion examination information in response to the input. Where deep learning was used to train the machine-learned model, the image or scan data is input directly. In other embodiments, one or more features are derived from the image or scan data and input.

The machine-learned model is a clinical decision support system. Machine learning uses training data of many hundreds or thousands of samples of inputs with labeled ground truth output or outputs for each sample. The training data is used as knowledge of past cases to train the classifier to generate the output for unseen cases. The training associates the features of the input vector with clinical decisions or other outputs in perfusion examination.

Any machine learning or training may be used. A probabilistic boosting tree, support vector machine, neural network, sparse auto-encoding classifier, Bayesian network, regression model, or other now known or later developed machine learning may be used. Any semi-supervised, supervised, or unsupervised learning may be used. Hierarchal or other approaches may be used. In one embodiment, the classification is by a machine-learned classifier learned with deep learning. As part of learning features that distinguish between different outcomes, the classifier is also machine trained to output based on the learned features.

In one embodiment, the deep learning is to train a machine-learned model to estimate the myocardial perfusion or other perfusion examination information. For example, each sample input vector includes CT perfusion sequential images, patient-specific information, and a value or values for one or more injection protocol parameters. The ground truth provided for each sample in the training data include a perfusion parametric image, color-map image, quantitative values such as peak value, time to peak, cerbal blood flow (CBF), and/or cerbal blood volume (CBV), and/or cardiologist or radiologist decision (e.g., diagnosis and/or therapy).

Any deep learning approach or architecture may be used. For example, a convolutional neural network is used. The network may include convolutional, sub-sampling (e.g., max pooling), fully connected layers, softmax, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided. Hierarchical structures are employed, either for learning features or representation or for classification or regression. The computer-based decision support system employs a machine learning algorithm for automated decision making.

In one embodiment, a recurrent neural network (RNN) is used. Since the perfusion data are sequential or temporal, the RNN model with a long-short term memory (LSTM) architecture may be used. This particular model may use the priori information to predict the enhancement or concentration values.

In another embodiment, a generative adversarial network (GAN) is used, such as an image-to-image or UNet generator and a CNN discriminator. Due to the sequential character of the perfusion information from sequential slices, deep learning-based GAN is trained to generate image from a fewer number of real perfusion images as compared to the regular CT perfusion. For example, spatial and/or temporal sparsity is provided in scanning. Instead of acquiring 10 scan shots for 10 real slices, the machine-learned model is trained by deep learning to generate perfusion for 10 slices based on input of only 4 temporal and/or spatial slices. The "synthetic" images produced by such a generative approach may or may not be used for visual analysis. For example, in an advantageous embodiment, the synthetic images generated by the trained GAN are used solely for the purpose of image analysis and subsequent quantification.

The machine-learned model, trained with or without deep learning, is trained to associate the categorical labels (output perfusion examination information) to the extracted values of one or more features from the input. The machine-learning uses training data with ground truth to learn to predict based on the input vector. The resulting machine-learned model defines how to extract values for features from the input and/or other features and output the perfusion examination information.

The input feature vector may include personalized or patient-specific information in addition to the CT data representing the contrast agents over time in the patient. To make sure any information manifested in the real CT perfusion measurements is not compromised for the new patient undergoing the examination, one or more values of the patient-specific information is provided in the training data and used in application of the machine-learned model. In application, the machine-learned model generates in response to input of the CT data and the patient-specific or personalized information. One or more values of a respective one or more injection protocol parameters may be used in training and application with or instead of the patient-specific information.

Due to the predictive nature of the machine-learned model, the machine-learned model may operate on sparse CT data showing perfusion. For example, the output is estimated from input of coronary CT data from no more than five scan shots. As another example, the output is estimated from CT data corresponding to no more than 100 CT dose index.

The machine-learned model outputs any perfusion examination information. The model provides individual measurement values or information of the regular CT perfusion examination. The machine-learned model may estimate the myocardial perfusion as a parametric image. A parametric perfusion image is generated. A quantity, such as data point values (e.g., intensity of return from contrast agents) or value of a perfusion curve of perfusion over time, is provided for each location. A grayscale or color-mapped image representing the values of the parameter (e.g., time to peak) as a function of location is generated by the machine-learned model.

The machine-learned model may estimate the myocardial perfusion as one or more quantities. For example, a peak value, time-to-peak, blood flow, blood volume, mean transit time, or combination thereof is output for a location, region, or perfusion field of view. Other quantitative values may be used.

The machine-learned model may generate a diagnosis and/or therapy as the perfusion examination information. The image processor, using the model, determines a diagnosis or therapy. The model is trained to generate the final diagnosis and/or decision as a "task-to-task" approach. Alternatively, the model is used to estimate the myocardial perfusion, and the image processor applies a threshold or look-up from the perfusion information to determine a diagnosis or therapy.

The diagnosis may be binary, such as whether the patient has a given disease. The diagnosis may be of a type of disease and/or level or extent of the disease, such as level of tissue death. The therapy may be the type of therapy, such as a recommendation for revascularization, stenting, bypass, or drug application. The therapy may be settings for a given type, such as recommending a specific stent or type of stent. The machine learning relates the inputs to the output diagnosis and/or therapy. Any cardiologist or radiologist decision may be output.

Figure 2:
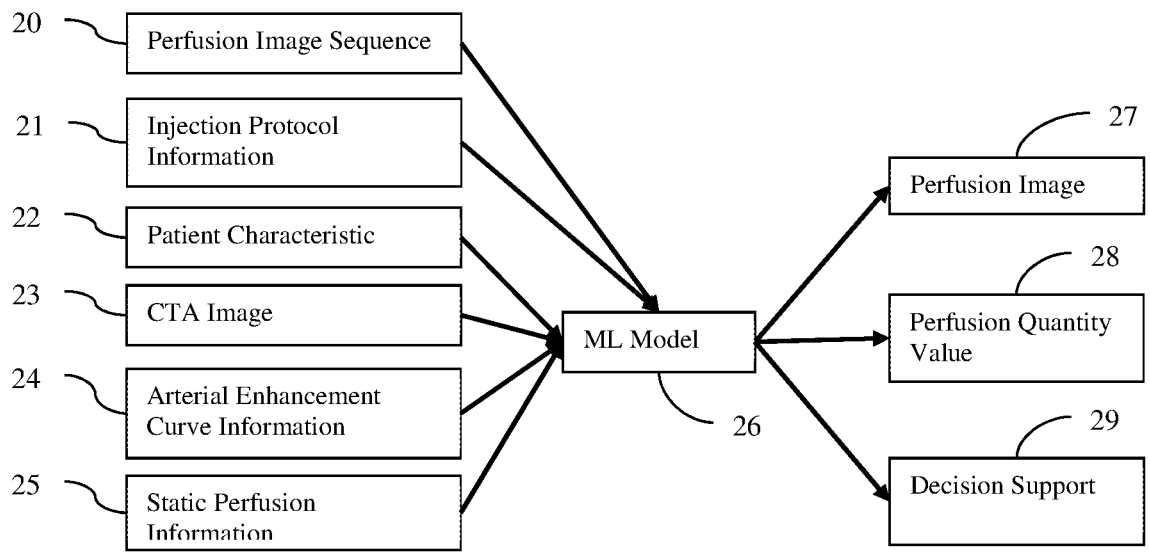
FIG. 2 illustrates an embodiment of generation of perfusion examination information from input of various types of information to a machine-learned model.

The same or different machine-learned models may output multiple perfusion examination information types. For example, perfusion images and/or quantifications are output as well as a clinical decision (e.g., therapy and/or diagnosis). The machine-learned model generates various types of information as the output in an "end-to-end" evaluation. FIG. 2 shows an example. Perfusion image sequence (e.g., CT data of contrast agent in the patient over time) 20, injection protocol information 21, patient-specific characteristics 22, CT angiography image 23 or values extracted therefrom, arterial enhancement curve information 24 and/or static perfusion information 25 are input to the machine-learned model 26. In response, the machine-learned model 26 outputs one or more perfusion images 27, perfusion quantity values 28, and/or decision support (e.g., diagnosis or therapy) 29.

In act 16, the perfusion examination information is transmitted. The transmission is to a display, such as a monitor, workstation, printer, handheld, or computer. Alternatively or additionally, the transmission is to a memory, such as a database of patient records, or to a network, such as a computer network. Other outputs of the perfusion examination information may be provided.

The transmission provides information for the physician decision. The clinical decision support system may provide an initial or starting recommendation, which may be approved or disapproved by the treating physician, and/or provides perfusion information (e.g., perfusion image and/or quantities) to be used to assist in diagnosis or therapy. The radiologist may use the perfusion examination information to determine what measures to perform or how much time to spend on any measures.

In one embodiment, the perfusion examination information, such as the myocardial perfusion, is visualized, either as text or in a graphical way (e.g. overlaid on the medical images) and presented to the clinician. One or more perfusion images generated by the machine-learned model may be displayed. The quantities for perfusion may be displayed. The decision support information, such as treatments, risks, guidelines, or other therapy or diagnosis information, may be output.

The machine-learned model is implemented locally. One advantage of a machine-learned model is that the online prediction is fast, outputting results almost instantaneously or in a matter of seconds given access to the input information. Hence, the machine-learned model may be run directly on the medical scanner or workstation located at a clinic or hospital. The system may be run on a portable device. Alternatively, the decision support system may be available as a service and/or operated remotely. A server or other remote processor is accessed by the hospital or clinician to obtain the perfusion examination information output.

Figure 3:
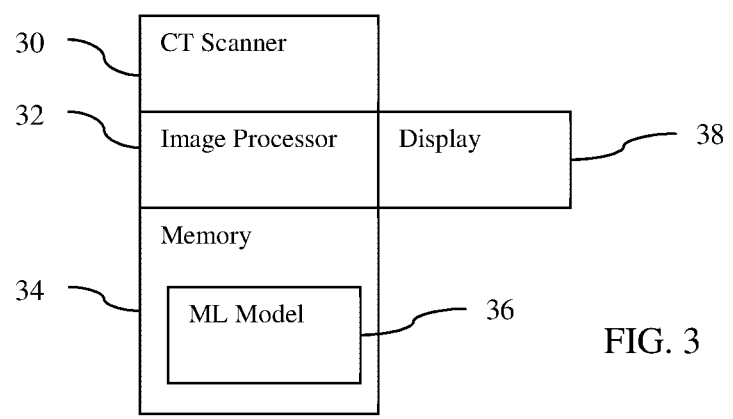
FIG. 3 is one embodiment of a system for decision support based on perfusion.

FIG. 3 shows a system for decision support based on perfusion in medical imaging. The system implements the method of FIG. 1, the arrangement of FIG. 2, or another method to output perfusion examination information. A machine-learned model 36 is used to generate the output given sparse CT data relative to a full sampling or standard perfusion imaging without a machine-learned model.

The system includes a CT scanner 30, an image processor 32, a memory 34, a display 38, and one or more machine-learned models 36. Additional, different, or fewer components may be provided. For example, a network or network connection is provided, such as for networking with a medical imaging network or data archival system or networking between the CT scanner 30 and the image processor 32. In another example, a user input is provided. As another example, a server is provided for implementing the image processor 32 and/or machine-learned models 36 remotely from the CT scanner 30.

The image processor 32, memory 34, display 38, and/or machine-learned models 36 are part of the CT scanner 30. Alternatively, the image processor 32, memory 34, display 38, and/or machine learned models 36 are part of an archival and/or image processing system, such as associated with a medical records database workstation or server, separate from the CT scanner 30. In other embodiments, the image processor 32, memory 34, display 38, and/or machine learned models 36 are a personal computer, such as desktop or laptop, a workstation, a server, or combinations thereof.

The CT scanner 30 is a medical diagnostic imaging CT system. A gantry supports a source of x-rays and a detector on opposite sides of a patient examination space. The gantry moves the source and detector about the patient to perform a CT perfusion scan. Various x-ray projections are acquired by the detector from different positions relative to the patient in a scan shot. Computed tomography solves for the two or three-dimensional distribution of the response from the projections. Ultrasound, x-ray, fluoroscopy, positron emission tomography, single photon emission computed tomography, and/or magnetic resonance systems may additionally or alternatively be used.

The CT scanner 30 is configured to scan for perfusion study. The scan is performed while contrast agent is within the patient. The CT scanner 30 is configured to output CT data for the patient as a sequence of images or data frames representing perfusion or the contrast agent over time. To reduce radiation dosage, the CT scanner 30 may be configured to sparsely sample the perfusion, such as using a sequence of six or fewer scan shots in total for imaging the contrast agent during a given study or injection. The patient may be subjected to 100 CT dose index or less. Greater dosage and/or number of scan shots may be used.

The memory 34 may be a graphics processing memory, a video random access memory, a random-access memory, system memory, cache memory, hard drive, optical media, magnetic media, flash drive, buffer, database, combinations thereof, or other now known or later developed memory device for storing data. The memory 34 is part of the CT scanner 30, part of a computer associated with the image processor 32, part of a database, part of another system, a picture archival memory, or a standalone device.

The memory 34 is configured to store data, such as in a computerized patient record. Any of the data discussed herein may be stored, such as the CT data, patient-specific information, and/or injection protocol parameter values. The memory 34 alternatively or additionally stores one or more machine-learned models 36. The memory 34 may alternatively or additionally store data during processing, such as storing information discussed herein or links thereto.

The memory 34 or other memory is alternatively or additionally a non-transitory computer readable storage medium storing data representing instructions executable by the programmed image processor 32 or a processor implementing the clinical decision support and/or machine-learned models 36. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 32 is a general processor, central processing unit, control processor, graphics processor, digital signal processor, three-dimensional rendering processor, application specific integrated circuit, field programmable gate array, digital circuit, analog circuit, combinations thereof, or other now known or later developed device for applying a clinical decision predictor. The image processor 32 is a single device or multiple devices operating in serial, parallel, or separately. The image processor 32 may be a main processor of a computer, such as a laptop or desktop computer, or may be a processor for handling some tasks in a larger system, such as in the CT scanner 30. The image processor 32 is configured by instructions, design, hardware, and/or software to perform the acts discussed herein.

The image processor 32 is configured generate perfusion examination information, such as estimate perfusion information. In response to input of the CT data with or without patient-specific information and/or the injection protocol parameter values to the machine-learned model 36, the perfusion examination information is output.

The machine-learned models 36 are implemented by the image processor 32 or other processor with access to the models 36 stored in the memory 34 or other memory. The machine-learned models 36 are defined as input channels (i.e., input vector), weights, relationships between weighted inputs or other layers, connections, filter kernels, and output channels.

The image processor 32, using the machine-learned model 36, is configured to estimate perfusion information by input of the CT data, the patient-specific information, and/or injection protocol information for injection of the contrast agent into the patient. The patient-specific information may be a patient attribute, an angiography image, an arterial enhancement curve, and/or quantification from the CT data. The output perfusion information may be a perfusion image, a quantitative value of perfusion, a diagnosis, and/or a therapy. The output is generated in response to input of CT data representing the contrast agent based on six or fewer scan shots and/or a 100 CT dose index or less.

The display 38 is a monitor, LCD, projector, plasma display, CRT, printer, or other now known or later developed devise for outputting visual information. The display 38 receives images of graphics, text, quantities, spatial distribution of anatomy or perfusion, or other information from the image processor 32, memory 34, CT scanner 30, or machine-learned models 36.

One or more images are displayed. The images may or may not include anatomical representation or imaging, such as an anatomical image from the CT data. The image includes the perfusion examination information, such as a perfusion image, a quantity, and/or clinical decision. The image includes an indication, such as a text, a graphic, or colorization, of the classification of the patient for perfusion study or examination.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for estimating myocardial perfusion by a medical imager, the method comprising:
scanning a patient with a computed tomography (CT) system using one or more injection protocol parameters that provide an effective dose corresponding to no more than 100 CT dose index, the scanning providing sparse coronary CT data representing contrast agent in a heart of the patient over time;
acquiring information for the patient in addition to the sparse coronary CT data;
estimating the myocardial perfusion by a machine-learned model having been trained by deep learning using training data comprising sequential CT images, associated injection protocol parameters, and associated patient specific information, the machine-learned model outputting the myocardial perfusion in response to input of the sparse coronary CT data, the one or more injection protocols, and the information; and
displaying the myocardial perfusion.

2. The method of claim 1 wherein scanning comprises scanning with fewer than five shots, and wherein estimating comprises estimating in response to input of the sparse coronary CT data from no more than the five shots.

3. The method of claim 1 wherein acquiring the information comprises acquiring patient attributes for the patient.

4. The method of claim 1 wherein acquiring the information comprises acquiring computed tomography angiography image of the patient.

5. The method of claim 1 wherein acquiring the information comprises acquiring an arterial enhancement curve information for the patient.

6. The method of claim 1 wherein acquiring the information comprises acquiring static myocardial measure for the patient.

7. The method of claim 1 wherein estimating comprises estimating the myocardial perfusion as a parametric image.

8. The method of claim 1 wherein estimating further comprises estimating the myocardial perfusion as a peak, time-to-peak, blow flow, blood volume, mean transit time, or combination thereof.

9. The method of claim 1 further comprising determining, by an image processor, a diagnosis or therapy from the estimated myocardial perfusion, and wherein displaying comprises displaying the diagnosis or therapy.

10. The method of claim 1 wherein estimating comprises estimating with the machine-learned model comprising a generative network having been trained adversarially to generate synthetic images from a fewer number of real perfusion images.

11. A system for decision support based on perfusion in medical imaging, the system comprising:
a computed tomography (CT) scanner for scanning a patient while contrast agent is in the patient using one or more injection protocol parameters that provide an effective dose corresponding to no more than 100 CT dose index, the CT scanner configured to output sparse CT data for the patient;

a memory configured to store a machine-learned model trained using training data comprising CT images and associated patient specific information;

an image processor configured to estimate perfusion information by input of the sparse CT data, the one or more injection protocol parameters, and patient-specific information to the machine-learned model, the perfusion information provided with no more than the six or fewer scan shots of the sparse CT data to represent the contrast agent; and a display configured to display the perfusion information.

12. The system of claim 11 wherein the patient-specific information comprises a patient attribute, an angiography image, an arterial enhancement curve, and/or quantification from the sparse CT data.

13. The system of claim 11 wherein the perfusion information comprises a perfusion image, a quantitative value of perfusion, a diagnosis, and/or a therapy.

14. A method for decision support based on perfusion measured by a medical imager, the method comprising:

scanning, using one or more injection protocol parameters that provide an effective dose corresponding to no more than 100 CT dose index, a patient with a computed tomography (CT) system, the scanning providing sparse CT data representing contrast agent in the patient over time;

generating perfusion examination information by a machine-learned model applied to the sparse CT data, the one or more injection protocols, and patient specific information; and outputting the perfusion examination information.

15. The method of claim 14 wherein generating comprises generating a diagnosis and/or therapy as the perfusion examination information.

16. The method of claim 14 wherein generating comprises generating by the machine-learned model comprising a deep-learned neural network applied to the sparse CT data and personalized patient information.

* * * * *